(12) United States Patent
Flank et al.

(10) Patent No.: US 7,952,710 B2
(45) Date of Patent: May 31, 2011

(54) SPECTROMETRIC ANALYSIS OF FLUIDS IN-SITU

(75) Inventors: William H. Flank, Chappaqua, NY (US); Sandra Glassman Flank, Chappaqua, NY (US); Sharon Flank, Washington, DC (US); Emil Walter Ciurczak, Golden's Bridge, NY (US); Carl Oppedahl, Dillon, CO (US)

(73) Assignee: Verrana LLC, Silver Spring, MD (US)

( * ) Notice: Subject to any disclaimer, the term of this patent is extended or adjusted under 35 U.S.C. 154(b) by 0 days.

(21) Appl. No.: 12/810,104

(22) PCT Filed: Mar. 4, 2009

(86) PCT No.: PCT/US2009/036056
§ 371 (c)(1),
(2), (4) Date: Jul. 25, 2010

(87) PCT Pub. No.: WO2009/111579
PCT Pub. Date: Sep. 11, 2009

(65) Prior Publication Data
US 2010/0309468 A1    Dec. 9, 2010

Related U.S. Application Data

(60) Provisional application No. 61/067,974, filed on Mar. 4, 2008, provisional application No. 61/038,229, filed on Mar. 20, 2008, provisional application No. 61/059,033, filed on Jun. 5, 2008.

(51) Int. Cl.
*G01J 3/28* (2006.01)
*G01J 3/42* (2006.01)
(52) U.S. Cl. .................... 356/326; 250/339.07
(58) Field of Classification Search .................. 356/319, 356/326, 328; 250/339.07, 339.08, 573, 250/576
See application file for complete search history.

(56) References Cited

U.S. PATENT DOCUMENTS 3,163,176 A * 12/1964 Darling ...................... 137/487.5
(Continued)

FOREIGN PATENT DOCUMENTS
WO    WO 2004/109262 A1 * 12/2004

OTHER PUBLICATIONS

International Search Report dated Aug. 31, 2009 from ISA—KR.

*Primary Examiner* — F. L Evans
(74) *Attorney, Agent, or Firm* — Oppedahl Patent Law Firm LLC

(57) ABSTRACT

A box 14 having a body 13 is used with a transparent flexible bag containing a liquid such as an IV bag. First and second faces 12 are positioned relative to each other. The faces each have therewithin an end or fiber optic port 11 of a respective light path. A light source is optically coupled with the light path of the first face and a spectrometer is optically coupled with the light path of the second face. The light paths are coaxial and are disposed so that the transparent flexible bag is positionable therebetween. The spectrometer is disposed to detect an anomaly in the liquid within the transparent flexible bag, and to annunciate the anomaly to a human user. The box defines a reproducible light path length through the liquid. A caliper 29 having a body 22 may be used in spectrometric analysis of a transparent tube containing a liquid such as a syringe or an IV line. The caliper has finger pads 27 which permit opening the spring-loaded caliper as needed. Rivets 25 provide a pivoting action relative to a pivot structure 21 which can also serve as a distance gauge. Compression spring 24 urges the caliper jaws together at lens locations 26. Lens locations 26 are optically coupled with internal fiber optic lines 28, and thence to external fiber optic connectors 23. A light source is optically coupled with one of the connectors 23 and a spectrometer is optically coupled with the other of the connectors 23.

4 Claims, 4 Drawing Sheets

U.S. PATENT DOCUMENTS

| | | | |
|---|---|---|---|
| 5,510,621 A * | 4/1996 | Goldman | 250/343 |
| 6,091,490 A | 7/2000 | Stellman | |
| 6,111,639 A * | 8/2000 | Reduto | 356/300 |
| 6,188,474 B1 | 2/2001 | Dussault | |
| 6,657,545 B1 * | 12/2003 | Lin et al. | 340/606 |
| 6,847,899 B2 * | 1/2005 | Allgeyer | 702/32 |
| 2005/0099624 A1 * | 5/2005 | Staehr et al. | 356/319 |
| 2005/0219540 A1 | 10/2005 | Haensch | |
| 2007/0142777 A1 | 6/2007 | Klein | |

\* cited by examiner

SPECTROMETRIC ANALYSIS OF FLUIDS IN-SITU

CROSS-REFERENCE TO RELATED APPLICATIONS

This patent application claims the benefit of U.S. application No. 61/038,229 filed Mar. 20, 2008, U.S. application No. 61/059,033 filed Jun. 5, 2008, and U.S. application No. 61/067,974 filed Mar. 4, 2008, each of which is hereby incorporated herein by reference for all purposes.

BACKGROUND

Counterfeiting and errors threaten patient safety. There are 1.25 million adverse reactions and 7,000 patient deaths annually in the United States as a result of drug errors. Existing verification relies largely on tagging and checking drug packaging. Of course, in a hospital setting, packaging and product are often separate.

Formulated medications created in the pharmacy, including but not limited to intravenous medication delivered in IV bags, pose a special challenge. Once the medicine or bag is made up, how do you tell whether it contains the proper medication, at the right concentration, and that the drug is both current and genuine? Opening the drug to sample it risks contaminating it.

For operating rooms, the identity of leftover waste drug is of concern. A hospital employee may try to steal leftover drugs and sell them, and substitute a substance such as saline or dextrose in the original container.

Immune globulin is often counterfeited.

Chemotherapy is expensive, as are antibiotics. Mistakes are even more expensive: an average lawsuit may cost nearly half a million dollars.

Patients may receive the wrong drug or the wrong dose, or an infused drug may spill or not be delivered correctly because of a blockage.

There is thus a great need for approaches to verify products in a hospital or long-term care environment. Such approaches need to be reliable, simple to use, and accurate. None of the prior-art approaches known to the applicants are completely satisfactory.

SUMMARY OF THE INVENTION

The present invention describes a verification system that works in the hospital or longterm care environment. The current invention verifies the product itself, checking for the correct medication, dosage, quality and purity, including a check for whether the drug is counterfeit.

The current invention, in its preferred embodiment, uses near-infrared spectroscopy (NIR) to look into the bag, including through the plastic, and tell in an instant whether it is right. The NIR shines a light on the substance and compares its optical components to a chemical library, a gold standard.

The present invention makes it possible to verify that the waste in a container is in fact the drug, not a substitute, without having to send it to a lab for analysis. The current invention includes hardware and software for a portable detection system that can tell in seconds whether the substance matches what it is expected to be. An advantage of the current invention in its portable embodiment is that it can be used by a nurse or technician on site, and does not need to be in a lab.

The present technique also checks for quality and purity, even allowing in-syringe verification.

The present invention makes it possible to check drugs as they leave the hospital pharmacy, and at later points as necessary.

Analytical chemical techniques such as near-infrared spectroscopy make it possible to monitor the drug once it has been compounded, through a syringe or IV bag, or even once it has entered the patient's body under the skin. Monitoring flow rate, as in this invention, offers new opportunities to keep patients safe.

A box 14 having a body 13 is used with a transparent flexible bag containing a liquid such as an IV bag. First and second faces 12 are positioned relative to each other. The faces each have therewithin an end or fiber optic port 11 of a respective light path. A light source is optically coupled with the light path of the first face and a spectrometer is optically coupled with the light path of the second face. The light paths are coaxial and are disposed so that the transparent flexible bag is positionable therebetween. The spectrometer is disposed to detect an anomaly in the liquid within the transparent flexible bag, and to annunciate the anomaly to a human user. The box defines a reproducible light path length through the liquid. A caliper 29 having a body 22 may be used in spectrometric analysis of a transparent tube containing a liquid such as a syringe or an IV line. The caliper has finger pads 27 which permit opening the spring-loaded caliper as needed. Rivets 25 provide a pivoting action relative to a pivot structure 21 which can also serve as a distance gauge. Compression spring 24 urges the caliper jaws together at lens locations 26. Lens locations 26 are optically coupled with internal fiber optic lines 28, and thence to external fiber optic connectors 23. A light source is optically coupled with one of the connectors 23 and a spectrometer is optically coupled with the other of the connectors 23.

BRIEF DESCRIPTION OF THE DRAWINGS

The invention will be described with respect to a drawing in several figures, of which.

Where possible, like elements have been depicted with like reference designations among the figures.

DETAILED DESCRIPTION

Figure 1:
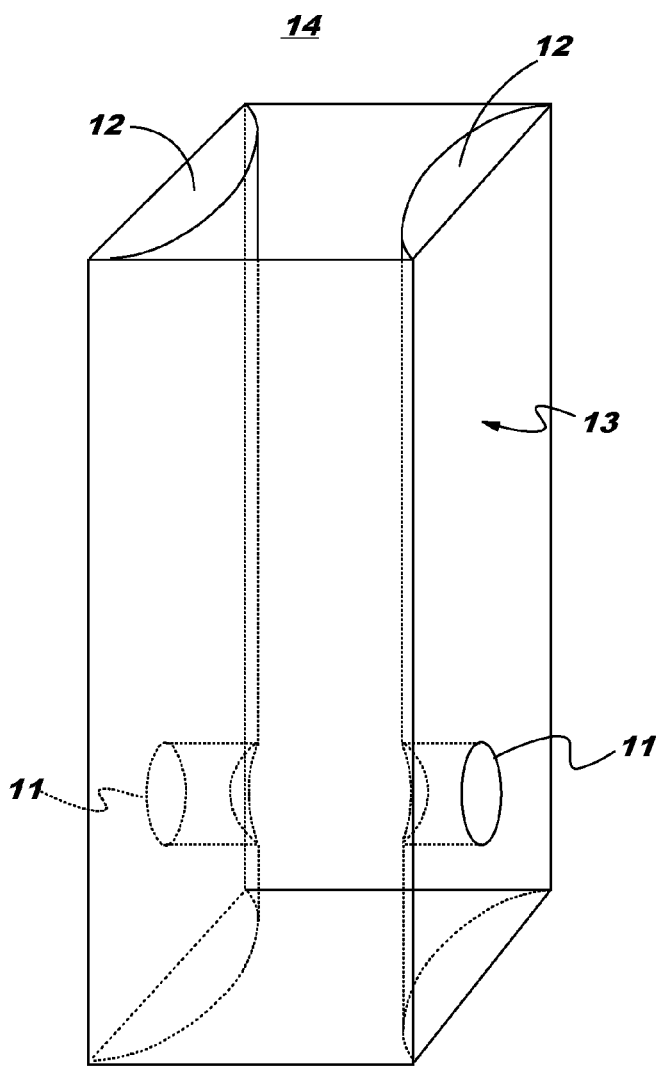
FIG. 1 is a perspective view of a box according to the invention.

A system and process is described in which a spectroscopic or similar instrumented technique, such as NIR, Raman IR, UV-VIS, x-ray, etc., suitably supported with identification, quantitation, diagnostic and control software, is used in operations where a substance or substances are being transported from one location to another, to identify the transported material, the rate at which the transfer is taking place, the amount of transfer accomplished during any given time interval, the recognition in some form of the transfer of a predetermined amount or amounts, the recognition in some form of a significant defined deviation from the expected integrated rate or rates of delivery, and similar such functions or operations as may be needed to more fully identify, quantify, monitor, control and communicate information relative to the said transfer operation. A further embodiment of this invention relates to the detection and monitoring of end-of-process and end-of-transfer progress, wherein failure and/or progress and/or completion of the process is confirmed and communicated. A further embodiment of this invention relates to processes and transformations whose component identities, properties, progress with respect to time and/or completion, etc., are monitored, communicated and controlled.

An example of an embodiment of this invention relates to the administration under monitored and/or controlled conditions of fluids and/or medications via gravity-driven or pumped intravenous infusion.

A further example relates to the detection and monitoring of fluids or medication delivery in vivo to allow positive confirmation at the end of the process of identity, rate and amount of substance transferred, e.g., at the tip of a needle as the substances enter the bloodstream.

A further example relates to the automated formulation or compounding of a mixture of materials, or material processing, whereby said process is under the control of a system capable of achieving said identification, monitoring, quantitation, control and information communication functions, wherein said system has had entered into it the requisite data necessary for such identification, monitoring, quantitation, control and information communication functions.

A further example relates to the monitoring and control of systems for sorting, dispensing or packaging of substances, wherein identity, properties, process rate and amount can be determined and communicated as needed, and records recorded thereof.

Additional developments include using a pair of fiber optic fibers inside the needle, which could send a beam and receive a spectral signal of what is coming out of the needle tip as it enters the bloodstream in the vein. This could allow an independent verification of flow, to supplement the empirical relating of concentration and flow with the signal obtained from under the skin, which may be attenuated to some extent from what comes down from the bag or the pump. The methodology would mimic an oximeter, where two wavelengths are used to monitor the oxygenated hemoglobin, with one of the wavelengths used to compensate for arterial pulsations.

The fibers may turn out to be all that is needed, and that might simplify the equipment involved. Micro-devices like cameras are used in arterial catheterization, for example, so there is precedent. Indeed, plain fibers would be simpler, and cheaper, and safer. The device could be frozen at a specific angle and actually be above the skin. This is similar to "interactance" measurements, used by USDA for meat. The skin acts as a natural scatterer of light, so there is a combination of reflection and absorption taking place.

If the fibers can spectroscopically look for the iron-porphyrin complex in hemoglobin as well as monitor the infusate, then with an audible signal one might also determine if the needle tip is approaching and entering a blood vessel. Vein-finding might thus become an integral part of the system. The hemoglobin has a red-NIR component, so either may be used (both are used in oximeters).

Micropressure sensing is an option, since suitable equipment might exist or be developed to monitor flow (or cessation of flow). Differential pressure measurement is an established method for measuring flow rates. This may be harder to use; awake patients normally have increased blood pressure due to an inherent dislike of needles and tension of receiving a drug.

The system may be employed in a hospital, long term care facility, or other health care environment to verify medication, checking for errors in dosage, concentration, medication, purity, and/or quality. It may be applied to formulated or compounded drugs. It may be applied to intravenous medication. It may be applied to medication in syringes. It may be applied to operating room waste or leftover medication.

Steps may include identification and/or confirmation of various infusate species, measurement of their concentrations and rates of flow, detection of leakages or blockages or changes in flow, and which may be coupled with a method for finding veins, where spectroscopic techniques, which can be of several kinds, including but not limited to ultraviolet, visible, near infrared, infrared, far infrared, Raman and other electromagnetic spectrum wavelengths in absorbance or reflectance mode, and can use double-beam methodologies, provide signals which can be processed to provide a variety of data outputs, including but not limited to instantaneous and integrated graphical displays, digital records of various kinds, visual and audible signals, etc.

A gold standard may be created, followed by checking other preparations against that gold standard.

One sequence of steps can be to test all the medications in a group and to identify outliers as potentially problematic.

It is also possible to use one or more optical fibers within the shaft of a needle used for infusion purposes, so that monitoring of one or more species occurs as the infusate leaves the tip of the needle inserted into a subject's vein or body. It is possible to monitor the changing signal intensity in a spectroscopic measurement to detect the changing proximity of hemoglobin in blood as a means of locating a vein or artery to be used for a particular purpose, including but not limited to infusion.

It is also possible to use a needle within a needle, or two needles alongside each other, such that one tube contains infusate and one or more optical fibers, and the other space is used to facilitate differential pressure measurements that will allow independent flow rate determinations to be made. This differential method is not limited to needles.

It is also possible to employ wireless signal transmission from one or more measurement units to a central console where continual signal sampling and processing will produce a variety of desired outputs.

Particular detailed embodiments of the invention will now be described.

Figure 2:
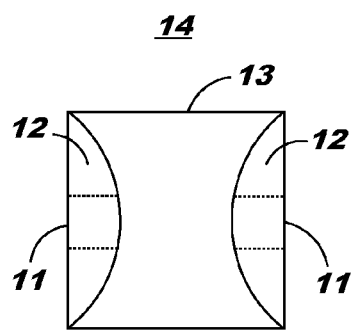
FIG. 2 is a top view of the box of FIG. 1.
Figure 3:
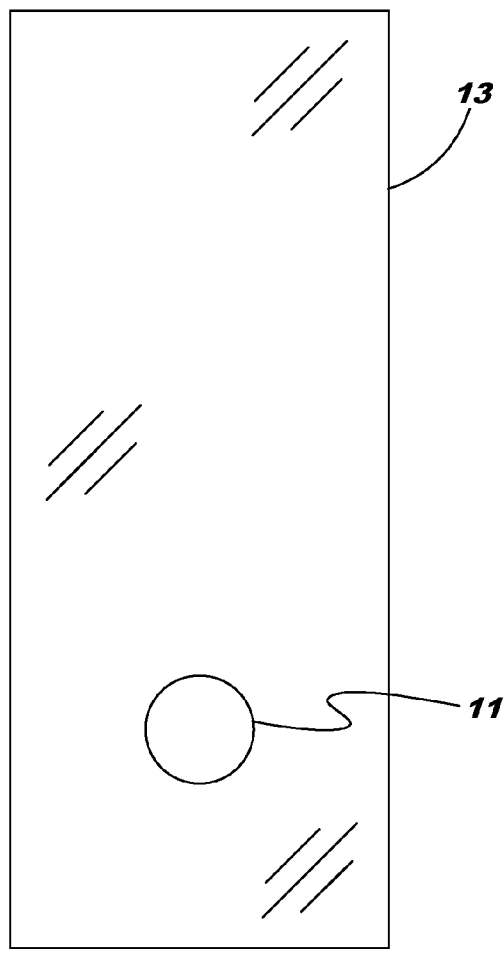
FIG. 3 is a side view of the box of FIG. 1.

A box 14 (FIGS. 1, 2, 3) having a body 13 is used with a transparent flexible bag containing a liquid such as an IV bag omitted for clarity in FIG. 1. First and second faces 12 are positioned relative to each other. The faces each have therewithin an end or fiber optic port 11 of a respective light path. A light source (omitted for clarity in FIG. 1) is optically coupled with the light path of the first face and a spectrometer (omitted for clarity in FIG. 1) is optically coupled with the light path of the second face. Typically the light paths are coaxial and are disposed so that the transparent flexible bag is positionable therebetween. Typically the spectrometer is disposed to detect an anomaly in the liquid within the transparent flexible bag, and to annunciate the anomaly to a human user. Typically the box defines a reproducible light path length through the liquid.

The box 14 may have a removable front face to allow for easier insertion and removal of the bag, as compared with stuffing the bag in from the top.

Figure 4:
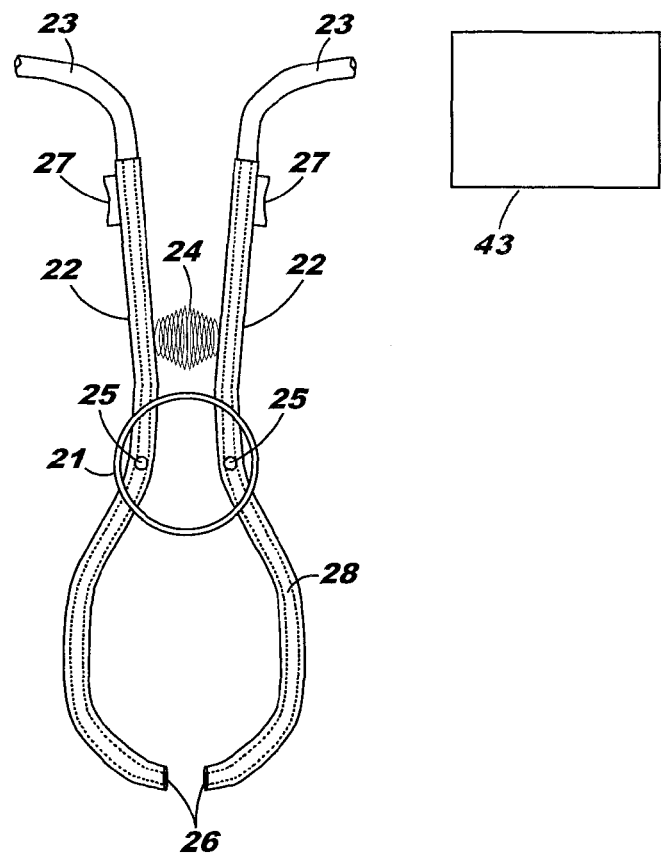
FIG. 4 shows a caliper according to the invention.

A caliper 29 (FIG. 4) having a body 22 may be used in spectrometric analysis of a transparent tube containing a liquid such as a syringe or an IV line. The caliper has finger pads 27 which permit opening the spring-loaded caliper as needed.

Rivets 25 provide a pivoting action relative to a pivot structure 21 which can also serve as a distance gauge. Compression spring 24 urges the caliper jaws together at lens locations 26. Lens locations 26 are optically coupled with internal fiber optic lines 28, and thence to external fiber optic connectors 23. A light source is optically coupled with one of the connectors 23 and a spectrometer 43 is optically coupled with the other of the connectors 23.

Figure 5:
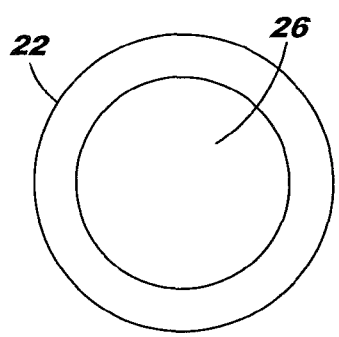
FIG. 5 shows a face on view of a lens location.
Figure 6:
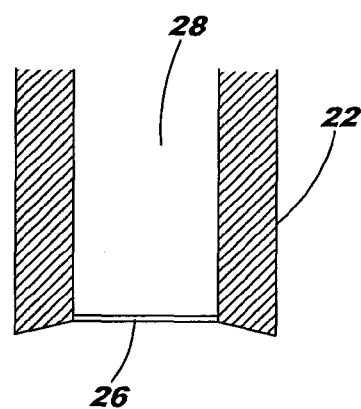
FIG. 6 shows a cross-sectional view of the lens location of FIG. 5.

FIG. 5 is a face-on view of the lens location 26 disposed within body 22. FIG. 6 is a cross-sectional view of the lens location 26 disposed within body 22, showing the internal fiber optic line 28. As may be seen the surface at 26 which engages the syringe or IV line has some concavity and thus can capture the syringe or IV line and keep it in place.

The distance gauge 21 comprises a sensor sensing the relative positions of the first and second jaws, and the sensor communicates to the spectrometer information indicative of a diameter of the transparent tube. The spectrometric analysis is carried out making use of the information indicative of the diameter of the transparent tube.

Figure 7:
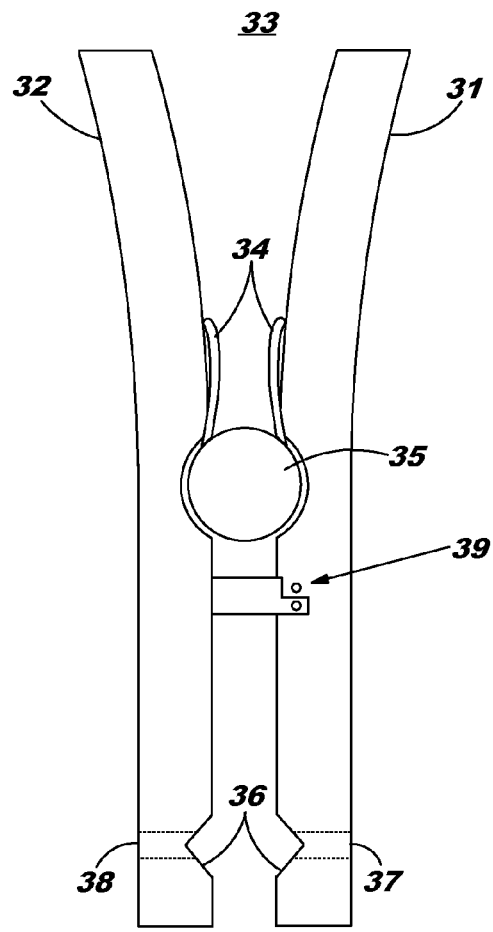
FIG. 7 shows a clip according to the invention.
Figure 8:
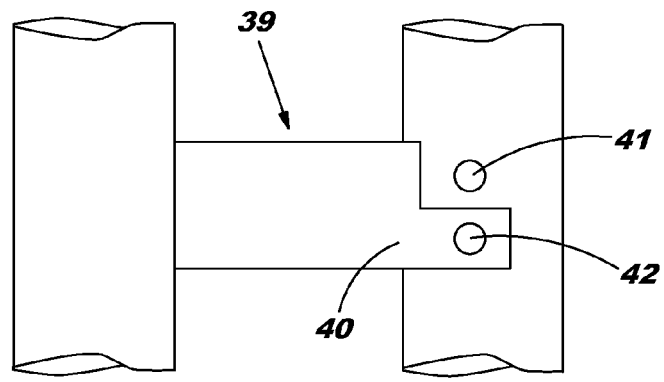
FIG. 8 shows a detail of a position or angle sensor according to the invention.

Another embodiment is shown in FIGS. 7 and 8 with clip 33. Jaws 36 are V-shaped and are dimensioned so as to provide reproducible positioning relative to cylinders or transparent tubes of some range of diameters. Light paths 37, 38 are positioned so that each light path impinges upon the transparent tube normal thereto, and so that the light paths are diametrically opposed across the transparent tube. Spring 34 urges the jaws 26 together relative to a hinge or pivot 35. Handles 31, 32 may be squeezed by a human operator to open the jaws 36. A sensor 39 is shown in more detail in FIG. 8. A movable piece 40 (attached to one of the jaws 26) moves relative to LED-phototransistor sensors 41, 42, offering perhaps three different discrete sensed signals depending on whether the jaws 36 are separated by a first distance, a second distance, or a third distance. In this way, if the cylinders are of any of three different standardized diameters, they may be disambiguated.

It will be appreciated that it is not crucial to use the particular sensing mechanism portrayed here.

The methods to be carried out may include the following.

The clip is clipped onto a transparent intravenous drip line with the transparent intravenous drip line seized within the groove of the first jaw and the groove of the second jaw. A liquid is passed through the transparent intravenous drip line and into a vein of a human being. After the clipping, light is passed through the light path of the groove of the first jaw, and through the transparent intravenous drip line and through the liquid, and through the light path of the groove of the second jaw, and to a spectrometer. A spectrometric analysis is carried out upon the light passing to the spectrometer. Later the clip is removed from the transparent intravenous drip line.

Alternatively the clip may be clipped onto a transparent syringe containing a liquid.

An IV bag may be placed into the box 14 and in contact with the opposed first and second faces 12. Light is passed through the light path of the first face, and through the transparent flexible bag and through the liquid, and through the light path of the second face, and to a spectrometer. A spectrometric analysis is carried out upon the light passing to the spectrometer. Later the the bag may be removed from the box. Still later the bag may be put to use in an intravenous drip, and some of the liquid may be passed into a vein of a human patient.

Those skilled in the art will have no difficulty devising myriad obvious improvements and variants without deviating in any way from the invention, all of which are intended to be encompassed within the claims which follow.

The invention claimed is:

1. A method for use with a transparent intravenous drip line, and for use with a clip having opposed first and second jaws urged toward each other, each jaw having a respective groove, the grooves opposing each other, each groove having therewithin an end of a respective light path, the method comprising the steps of:
    clipping the clip onto the transparent intravenous drip line with the transparent intravenous drip line seized within the groove of the first jaw and the groove of the second jaw;
        wherein the transparent intravenous drip line is cylindrical in cross section and the light paths are disposed relative to the grooves so that each light path impinges upon the drip line normal thereto, and so that the light paths are diametrically opposed across the transparent intravenous drip line;
    passing a liquid through the transparent intravenous drip line and into a vein of a human being;
    after the clipping, passing light through the light path of the groove of the first jaw, and through the transparent intravenous drip line and through the liquid, and through the light path of the groove of the second jaw, and to a spectrometer, and carrying out a spectrometric analysis upon the light passing to the spectrometer;
        wherein the clip further comprises a sensor sensing the relative positions of the first and second jaws, wherein the sensor communicates to the spectrometer information indicative of a diameter of the transparent intravenous drip line, and wherein the spectrometric analysis is carried out making use of the information indicative of the diameter of the transparent intravenous drip line; and
    removing the clip from the transparent intravenous drip line.

2. A method for use with a transparent syringe containing a liquid, and for use with a clip having opposed first and second jaws urged toward each other, each jaw having a respective groove, the grooves opposing each other, each groove having therewithin an end of a respective light path, the method comprising the steps of:
    clipping the clip onto the transparent syringe with the transparent syringe seized within the groove of the first jaw and the groove of the second jaw;
    after the clipping, passing light through the light path of the groove of the first jaw, and through the transparent syringe and through the liquid, and through the light path of the groove of the second jaw, and to a spectrometer, and carrying out a spectrometric analysis upon the light passing to the spectrometer;
        wherein the transparent syringe is cylindrical in cross section and the light paths are disposed relative to the grooves so that each light path impinges upon the syringe normal thereto, and so that the light paths are diametrically opposed across the transparent syringe; and
        wherein the clip further comprises a sensor sensing the relative positions of the first and second jaws, wherein the sensor communicates to the spectrometer information indicative of a diameter of the transparent syringe, and wherein the spectrometric analysis is carried out making use of the information indicative of the diameter of the transparent syringe; and
    removing the clip from the transparent syringe.

3. Apparatus for use in spectrometric analysis of a transparent tube containing a liquid, the apparatus comprising:
    a clip having opposed first and second jaws urged toward each other, each jaw having a respective groove, the grooves opposing each other, each groove having therewithin an end of a respective light path;

a light source optically coupled with the light path of the groove of the first jaw;

wherein the clip further comprises a sensor sensing the relative positions of the first and second jaws, wherein the sensor communicates to the spectrometer information indicative of a diameter of the transparent tube, and wherein the spectrometric analysis is carried out making use of the information indicative of the diameter of the transparent tube; and a spectrometer optically coupled with the light path of second jaw.

4. Apparatus for use in spectrometric analysis of a transparent tube containing a liquid, the apparatus comprising:

a clip having opposed first and second jaws urged toward each other, each jaw having a respective groove, the grooves opposing each other, each groove having therewithin an end of a respective light path;

wherein the clip further comprises a sensor sensing the relative positions of the first and second jaws, wherein the sensor communicates external to the clip information indicative of a diameter of the transparent tube;

a connection point for a light source, the connection point optically coupled with the light path of the groove of the first jaw;

a connection point for a spectrometer, the connection point optically coupled with the light path of second jaw.

* * * * *